(12) United States Patent
Dirisio et al.

(10) Patent No.: US 10,675,059 B2
(45) Date of Patent: Jun. 9, 2020

(54) DYNAMIC DECOMPRESSIVE CRANIOTOMY FIXATION DEVICES AND RELATED METHODS

(71) Applicant: ALBANY MEDICAL COLLEGE, Albany, NY (US)

(72) Inventors: Darryl J. Dirisio, Slingerlands, NY (US); Parvez Memet Shaikh, Morgantown, WV (US); John C. Dalfino, Rensselaer, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 584 days.

(21) Appl. No.: 15/367,984

(22) Filed: Dec. 2, 2016

(65) Prior Publication Data

US 2017/0079685 A1 Mar. 23, 2017

Related U.S. Application Data

(63) Continuation of application No. PCT/US2014/040500, filed on Jun. 2, 2014.

(51) Int. Cl.
*A61B 17/68* (2006.01)
*A61B 17/80* (2006.01)

(52) U.S. Cl.
CPC ............ *A61B 17/688* (2013.01); *A61B 17/80* (2013.01); *A61B 17/8023* (2013.01);
(Continued)

(58) Field of Classification Search
CPC .......... A61B 17/688; A61B 2017/8023; A61B 2017/681; A61B 17/663; A61B 17/8071;
(Continued)

(56) References Cited

U.S. PATENT DOCUMENTS

| | | | |
|---|---|---|---|
| 5,578,036 | A | 11/1996 | Stone et al. |
| 5,707,373 | A | 1/1998 | Sevrain et al. |

(Continued)

OTHER PUBLICATIONS

International Search Report and Written Opinion issued in PCT Application PCT/US2014/040500 dated Oct. 23, 2014.

*Primary Examiner* — David W Bates
(74) *Attorney, Agent, or Firm* — Heslin Rothenberg Farley & Mesiti P.C.

(57) ABSTRACT

The present disclosure provides dynamic cranial fixation devices and related methods for attaching a resected bone portion(s), or a bone flap, to the skull in such a manner that allows for brain swelling to occur with minimal constraint following a craniotomy or craniectomy. The present disclosure provides dynamic cranial fixation devices and related methods that provide outward movement of the bone flap as the brain swells underneath the bone flap to prevent or reduce a rise in the intracranial pressure. Once the brain swelling resolves, the dynamic cranial fixation devices and related methods of the present disclosure allow the bone flap to return to its original position (before resection) without further surgery, implantation or the like. Once the bone flap return to its original position (or substantially similar position), the bone flap may fuse with the neighboring bone(s), potentially with the assistance of one or more fusion aid.

20 Claims, 9 Drawing Sheets

(52) U.S. Cl.
CPC ...... *A61B 17/8061* (2013.01); *A61B 17/8085* (2013.01); *A61B 2017/681* (2013.01)

(58) Field of Classification Search
CPC ............. Y10S 606/903; Y10S 606/904; Y10S 606/905; A61F 2220/091
USPC .......................................................... 606/70
See application file for complete search history.

(56) References Cited

U.S. PATENT DOCUMENTS

| | | | |
|---|---|---|---|
| 5,769,850 A * | 6/1998 | Chin .................... | A61B 17/171 606/102 |
| 5,800,436 A | 9/1998 | Lerch et al. | |
| 5,855,580 A * | 1/1999 | Kreidler ............... | A61B 17/663 606/282 |
| 5,902,304 A * | 5/1999 | Walker ................. | A61B 17/663 606/282 |
| 5,916,200 A | 6/1999 | Eppley et al. | |
| 5,916,217 A | 6/1999 | Manthrop et al. | |
| 6,277,124 B1 * | 8/2001 | Haag .................... | A61B 17/663 606/105 |
| 6,355,036 B1 * | 3/2002 | Nakajima ............... | A61B 17/66 606/54 |
| 6,379,363 B1 | 4/2002 | Herrington et al. | |
| 6,485,493 B1 | 11/2002 | Bremer et al. | |
| 6,685,707 B2 | 2/2004 | Roman et al. | |
| 6,706,070 B1 | 3/2004 | Wagner et al. | |
| 6,755,834 B2 | 6/2004 | Amis et al. | |
| 7,048,737 B2 | 5/2006 | Wellisz et al. | |
| 7,361,178 B2 | 4/2008 | Hearn et al. | |
| 7,387,633 B2 | 6/2008 | Ahmad et al. | |
| 7,875,033 B2 * | 1/2011 | Richter .................. | A61B 17/66 606/280 |
| 8,257,355 B2 * | 9/2012 | Chin .................... | A61B 17/7058 606/281 |
| 8,439,956 B2 | 5/2013 | Ko et al. | |
| 9,468,703 B2 * | 10/2016 | Khanna ................ | A61B 17/688 |
| 9,956,015 B2 * | 5/2018 | Ehmke .................. | A61B 17/80 |
| 10,111,757 B2 * | 10/2018 | Abdou .................... | A61F 2/447 |
| 10,524,844 B2 * | 1/2020 | Hearn .................. | A61B 17/8009 |
| 2002/0035368 A1 * | 3/2002 | Schumacher ........ | A61B 17/663 606/86 R |
| 2002/0156485 A1 * | 10/2002 | Sellers .................. | A61B 17/663 606/105 |
| 2003/0105463 A1 * | 6/2003 | Wolgen ................ | A61B 17/663 606/71 |
| 2003/0163132 A1 * | 8/2003 | Chin .................. | A61B 17/7059 606/280 |
| 2003/0229348 A1 * | 12/2003 | Sevrain .............. | A61B 17/7059 606/70 |
| 2004/0102773 A1 * | 5/2004 | Morrison ........... | A61B 17/7059 606/288 |
| 2005/0216008 A1 * | 9/2005 | Zwirnmann ........... | A61B 17/68 606/281 |
| 2005/0234448 A1 * | 10/2005 | McCarthy .......... | A61B 17/8004 606/57 |
| 2007/0233094 A1 * | 10/2007 | Colleran ............ | A61B 17/7007 606/86 A |
| 2007/0270820 A1 * | 11/2007 | Dickinson .......... | A61B 17/7007 606/279 |
| 2007/0276371 A1 * | 11/2007 | Baynham .......... | A61B 17/7059 606/86 A |
| 2008/0200954 A1 * | 8/2008 | Tucci .................... | A61B 17/688 606/280 |
| 2008/0300635 A1 * | 12/2008 | Lieponis ........... | A61B 17/7059 606/280 |
| 2008/0311542 A1 * | 12/2008 | Rana .................. | A61B 17/663 433/140 |
| 2010/0075270 A1 * | 3/2010 | Figueroa .............. | A61B 17/663 433/18 |
| 2010/0094428 A1 * | 4/2010 | Ralph .................. | A61B 17/688 623/17.19 |
| 2010/0121328 A1 * | 5/2010 | Reitzig .............. | A61B 17/7059 606/71 |
| 2010/0228291 A1 * | 9/2010 | Butler ................ | A61B 17/7059 606/259 |
| 2011/0028972 A1 | 2/2011 | Khanna | |
| 2011/0106082 A1 * | 5/2011 | Kave .................... | A61B 17/708 606/70 |
| 2011/0288645 A1 * | 11/2011 | Braddock, Jr. ....... | A61F 2/4425 623/17.16 |
| 2012/0259344 A1 * | 10/2012 | Johnston, Jr. .......... | A61B 17/66 606/105 |
| 2012/0277749 A1 * | 11/2012 | Mootien ............... | A61B 17/666 606/70 |
| 2013/0282011 A1 * | 10/2013 | Brogan ................ | A61B 17/688 606/75 |
| 2014/0012324 A1 * | 1/2014 | Bullard .............. | A61B 17/8023 606/279 |
| 2014/0148812 A1 * | 5/2014 | Harris .................... | A61B 17/66 606/90 |
| 2014/0277175 A1 * | 9/2014 | Campbell ............ | A61B 17/809 606/281 |
| 2015/0025587 A1 * | 1/2015 | Kim .................... | A61B 17/663 606/282 |
| 2015/0141926 A1 * | 5/2015 | Asaad .................... | A61M 25/02 604/175 |
| 2015/0209093 A1 * | 7/2015 | Dallis ................ | A61B 17/8023 606/281 |
| 2015/0272644 A1 * | 10/2015 | Noon ................ | A61B 17/8009 606/90 |
| 2018/0092663 A1 * | 4/2018 | Gordon .................. | A61B 17/66 |

* cited by examiner

DYNAMIC DECOMPRESSIVE CRANIOTOMY FIXATION DEVICES AND RELATED METHODS

CROSS REFERENCE TO RELATED APPLICATIONS

This application is a continuation of PCT Application No. PCT/US2014/040500 filed on Jun. 2, 2014, the entirety of which is hereby expressly incorporated by reference in its entirety, and the priority of which is hereby claimed.

BACKGROUND

The present disclosure generally fixation devices for cranial bones, and in particular to dynamic decompressive craniotomy fixation devices and related methods.

Increased intracranial pressure can follow traumatic brain injuries, strokes, tumors or other injuries, ailments or the like. When increased intracranial pressure presents an obstacle to simple maneuvers, such as head elevation, sedation, or osmotic diuretics (mannitol), then consideration should be given towards performing a decompressive craniotomy or craniectomy for example. Other factors, issues, preferences or considerations may also lead to the need or desire to perform a decompressive craniotomy or craniectomy. This potentially lifesaving procedure is being performed at an increased rate.

Decompressive craniotomy or craniectomy is a neurosurgical procedure used to alleviate elevated intracranial pressure due to brain swelling. Typically, a portion of the cranium over the affected area of the patient's brain is removed and at least a portion of the dura of the brain is thereby fenestrated to accommodate the swollen portion of the brain and reduce the intracranial pressure. Once the bone portion(s) is/are removed, the compromised cranium is left "open" for a period of time ranging from a few weeks to potentially several months to allow a sufficient amount of swelling to dissipate. During that time, there typically is a change in the cerebral spinal fluid (CSF) dynamics of the patient, which can result in hydrocephalus or CSF leakage for example. CSF leakage, in particular, may increase infection risk.

Replacement of the removed portion(s) of the cranium or skull plate after decompressive craniotomy or craniectomy as soon as medically safe, possible or advantageous is often desirable, such as in consideration of the alteration of the CSF dynamics as discussed above, risk of brain injury due to the compromised cranium, and cosmesis purposes. Once brain swelling is resolved, the removed bone portion(s) or flap(s), or a replacement thereof, is typically fixed to the skull to close the skull via another procedure to surgery.

Decompressive hinge craniotomy or craniectomy, where the portions(s) of bone or the bone plate is not removed, is gaining more acceptance as a safer alternative to the temporary complete removal of bone or a cone plate during a typical decompressive craniotomy or craniectomy. Decompressive hinge craniotomy or craniectomy may reduce the risks associated with complete removal of bone for an extend period of time, as discussed above.

Decompressive hinge craniotomy or craniectomy typically involves removing or disconnecting a section of cranial bone or bone plate over or about the affected area of a patient's brain, and then attaching or coupling the removed or disconnected bone with a device or mechanism at least generally into its original position. The device(s) or mechanism(s) may allow the removed or disconnected bone or bone plate to shift in one direction with respect to the skull. For example, the device(s) or mechanism(s) may allow the removed or disconnected bone or bone plate to translate in an outward direction away from the brain as the brain swells to reduce the intracranial pressure.

Once the brain swelling is resolved, the device(s) or mechanism(s) used to attach or couple the disconnected or removed bone plate to the skull and dynamically allow for brain swelling should ideally allow the bone plate to return to its original position for permanent fixation without the requirement of further surgery. Considering the state of the art that exists today, there is a need for better devices and methods for cranial fixation that would allow optimal, dynamic immediate treatment of increased intracranial pressure, and obviate the need for a fixation reoperation after the increased intracranial pressure subsides.

SUMMARY OF THE INVENTION

The present disclosure relates to dynamic cranial stabilization and fixation devices and related methods for attaching a resected bone portion(s), or bone flap, to the skull in such a manner that allows for brain swelling to occur with minimal constraint following a craniotomy or craniectomy. The present disclosure provides for outward movement of the bone flap as the brain swells underneath the bone flap to prevent or reduce a rise in the intracranial pressure (ICP). Once the brain swelling resolves, the dynamic cranial stabilization and fixation devices and related methods of the present disclosure may allow the bone flap to return to its original position (before resection) without further surgery, implantation or the like. Once the bone flap to return to its original position (or substantially similar position), the bone flap may fuse with the neighboring skull bone(s) (potentially with the assistance of one or more fusion aid).

In one aspect, the present disclosure provides a dynamic cranial fixation device for coupling a bone flap and a cranium. The device includes a connector member, a first wing member, and a second wing member. The connector member includes a first end and a second end. The first wing member includes a first pair of apertures configured to accept a bone attachment member therethrough to fix the first wing member to a cranium. The first wing member is rotatably coupled to the first end of the connector member. The second wing member includes a second pair of apertures configured to accept a bone attachment member therethrough to fix the second wing member to a bone flap. The second wing member also includes an elongated aperture. The second end of the connector member is provided within the elongated aperture of the second wing member to movably couple the second wing member with the connector member.

In another aspect, the present disclosure provides a dynamic cranial fixation device for coupling a bone flap and a cranium. The device includes a connector member, a first wing member, and a second wing member. The first wing member includes at least a first aperture configured to accept a bone attachment member therethrough to fix the first wing member to one of a bone flap and a cranium. The first wing member extends from a first side of the connector member. The second wing member includes at least a first aperture configured to accept a bone attachment member therethrough to fix the second wing member to the other of the bone flap and the cranium as compared to the first wing member. The second wing member extends from a second side of the connector member. The connector member includes an elongated aperture or a pair of pin members, and each of the first and second wing members include the other of the elongated aperture or one of the pin members of the pair of pin members as compared to the connector member. The pin members are provided within the elongated aperture to movably couple the first and second wing members with the connector member.

These and other objects, features and advantages of this disclosure will become apparent from the following detailed description of the various aspects of the disclosure taken in conjunction with the accompanying drawings.

DETAILED DESCRIPTION

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure relates to dynamic cranial stabilization and/or fixation devices and related methods for attaching a resected bone portion(s), or bone flap, to the skull in such a manner that allows for brain swelling to occur with minimal constraint following a craniotomy or craniectomy. The present disclosure provides for outward movement of the bone flap as the brain swells underneath the bone flap to prevent or reduce a rise in the intracranial pressure (ICP). Once the brain swelling resolves, the dynamic cranial stabilization and fixation devices and related methods of the present disclosure may allow the bone flap to return to its original position (before resection) without further surgery, implantation or the like. Once the bone flap to return to its original position (or substantially similar position), the bone flap may fuse with the neighboring bone(s) (potentially with the assistance of one or more fusion aid).

Figure 1A:
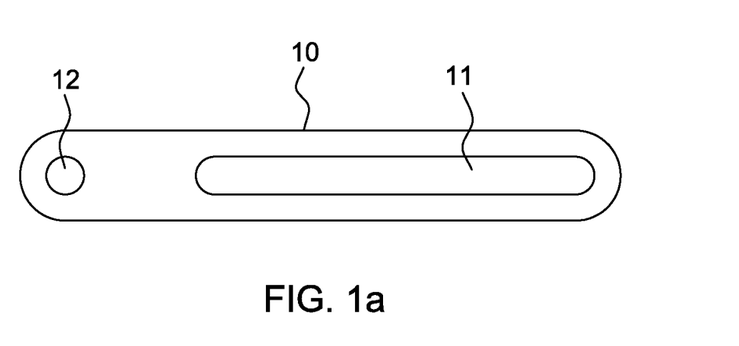
FIG. 1a is a top view of an exemplary embodiment of a dynamic decompressive cranial fixation device according to the present disclosure.
Figure 1B:
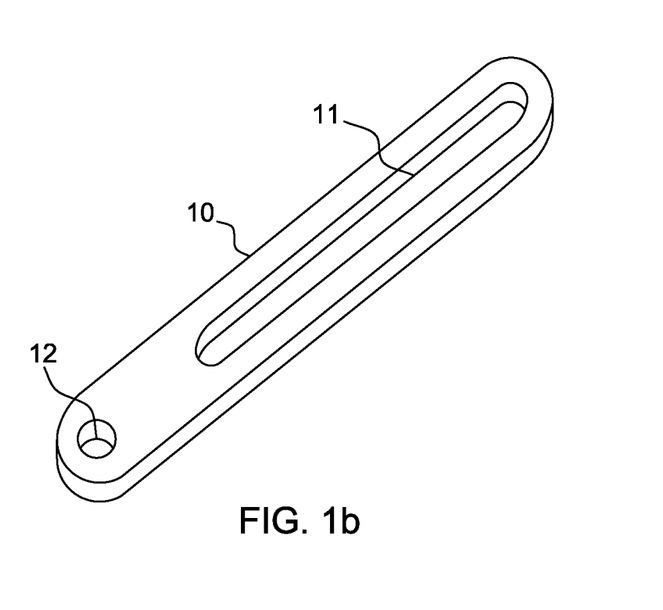
FIG. 1b is a perspective view of the dynamic decompressive cranial fixation device of FIG. 1a according to the present disclosure.

FIGS. 1a & 1b illustrate one embodiment of a dynamic cranial stabilization and/or fixation device 10 and related method. The elongate device 10 may be relatively flat and include a first fixation aperture 12 and second dynamic aperture or slot 11. The device may be made from any material, such as one or more materials that are compatible with the human body for implantation or coupling therewith.

In some embodiments the device 10 may be made from at least one metal and/or a polymer.

The first and second apertures 12, 11 may be sized, shaped and otherwise configured to accept or mate with an attachment member, such as a screw, pin, nail or the like. The first and second apertures 12, 11 may be positioned at opposing ends or sides of the device 10. The attachment member may be configured to attach couple, fix or otherwise securely mate with cranial bone. The first aperture 12 may be configured to prevent substantially movement of the device 10 with respect to an attachment member extending through the first aperture 12. As the attachment member may be fixed to a first bone, the first aperture 12 may be configured to prevent substantial movement of the device 10 with respect to the first bone. Stated differently, as the attachment member may be fixed to a first bone, the first aperture 12 and an attachment member may be configured to prevent substantial movement of first bone with respect the device 10.

The second aperture 11 may be configured to substantially allow movement of the device 10 with respect to an attachment member extending through the second aperture 11. As shown in FIGS. 1*a* and 1*b*, the second aperture 11 may be elongate such that the second aperture 11 is substantially larger than an attachment member extending therethrough at least in a first direction. In this way, the device 10 may be capable of translating along the dynamic second aperture 11 about an attachment member extending therethrough. As the attachment member may be fixed to a second bone, such as a bone flap, and the device 10 may be fixed to a first bone (e.g., part of a cranium), the second bone flap may be moveable with respect to the device 10 and the first bone (as discussed further below with respect to FIGS. 2*a* and 2*b*). Stated differently, the second aperture 11 of the device 10 may allow for outward and/or inward extension of a bone flap with respect to the device and the bone in which the first aperture 12 is fixed (and another aperture and corresponding bone). The size, shape or other configuration metric of the dynamic second aperture 11 may thereby control or dictate the amount, degree, direction and/or path of the bone flap with respect to the first bone. The term "bone flap" is used herein to refer to any material utilized to cover, protect, abut and/or shield an area or portion of a patient which was exposed by removal of a portion of the cranium or skull. The "bone flap" may be bone, cartilage, tissue or any other "living" material, and prosthetic or artificial bone material, such as metal or polymer, and combination thereof. It is noted that the orientation of the device 10 (and the other devices disclosed herein) may be reversed such that the first aperture(s) 12 is utilized to fix the device 10 to a bone flap, and the second aperture(s) 11 is utilized to dynamically couple the device 10 to the cranium such that both the bone flap and the device 10 are able to translate or move with respect to the cranium.

Figure 1C:
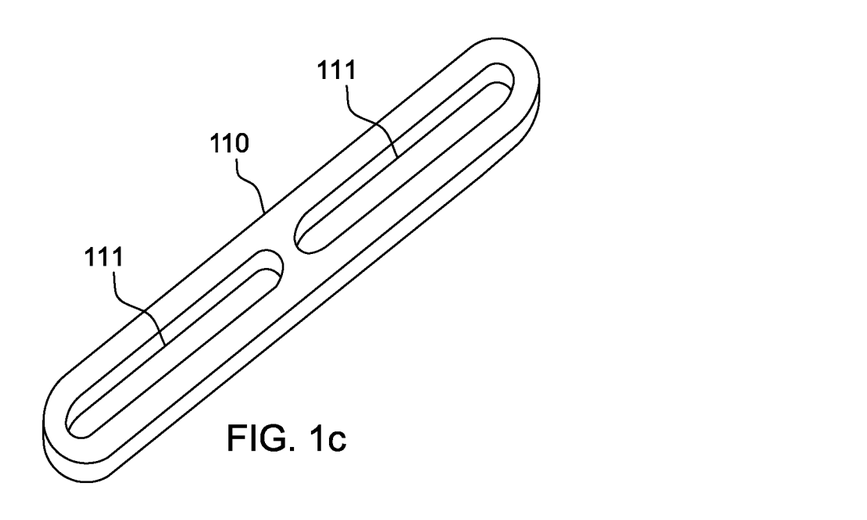
FIG. 1c is a perspective view of another embodiment of a dynamic decompressive cranial fixation device according to the present disclosure.

FIG. 1*c* illustrates another embodiment of a dynamic cranial stabilization and/or fixation device 110 and related method. The cranial fixation device 110 is similar to the cranial fixation device 10 described above and therefore like reference numerals preceded by the numeral "1" is used to indicate like elements. The cranial fixation device 110 includes two apertures 111, 111 that each may be configured to substantially allow movement of the device 110 with respect to an attachment member extending through the other of the two apertures 111, 111 and an attachment member extending therethrough, as shown in FIG. 1*c*. As shown in FIG. 1*c*, the apertures 111, 111 may be elongate such that they are substantially larger than an attachment member extending therethrough at least in a first direction.

In this way, the device 110 may be capable of translating along the apertures 111, 111 about an attachment member extending therethrough. As one of the attachment members may be fixed to a bone flap through one of the apertures 111, and another attachment member may be fixed to a first bone (e.g., part of a cranium) through the other of the apertures 111, the bone flap may be moveable with respect to the device 110, the first bone, and the attachment member in first bone. Still further, the device 110 may be movable with respect to the attachment members, the bone flap, and the second bone. Stated differently, the apertures 111 of the device 110 may allow for outward and/or inward extension of a bone flap with respect to the device 110, the first bone, and the attachment member extending through one of the apertures 111 and into the first bone. However, as the two apertures 111, 111 are separate and distinct, the total travel or translation of the device 110 with respect to the attachment members, first bone, and the bone flap may be limited by the sizes or lengths of the apertures 111, 111.

Figure 1D:
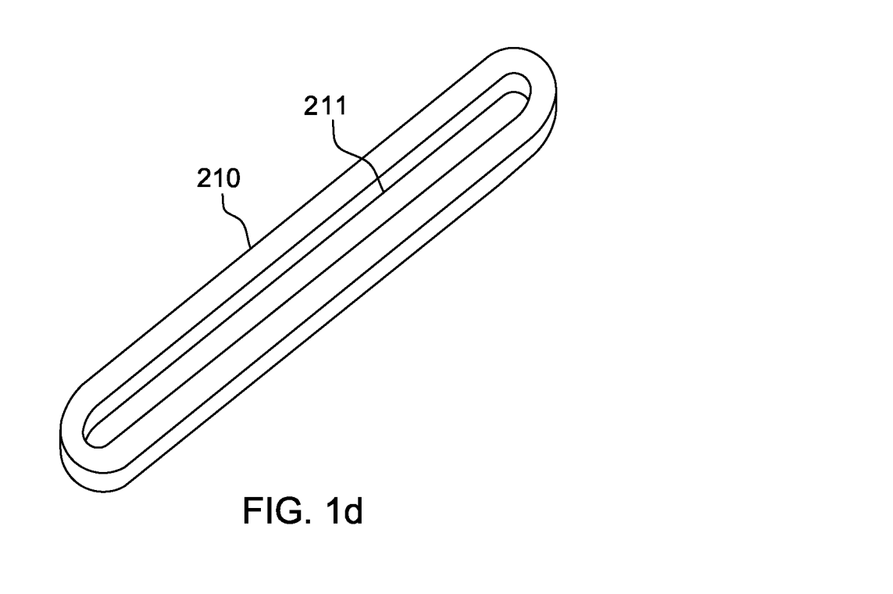
FIG. 1d is a perspective view of another embodiment of a dynamic decompressive cranial fixation device according to the present disclosure.

FIG. 1*d* illustrates another embodiment of a dynamic cranial stabilization and/or fixation device 210 and related method. The cranial fixation device 210 is similar to the cranial fixation devices 10 and 110 described above and therefore like reference numerals preceded by the numeral "2", as opposed to "1" for example, is used to indicate like elements. Device 210 includes a single elongated aperture or screw hole 211 extending along at least the majority of the length of the device 210. At least two attachment members may be coupled through the singular aperture 211, such as one onto a cranial bone and one into a bone flap. The elongated aperture 111 may thereby allow movement of the bone flap with respect to the device 210, cranial bone, and attachment member in the cranial bone as explained above. Further, because the at least two attachment members are positioned within the same aperture 211, the device 210 may, depending upon the particular configuration, allow for a greater amount of movement or translation of the bone flap as compared to other devices.

Figure 1E:
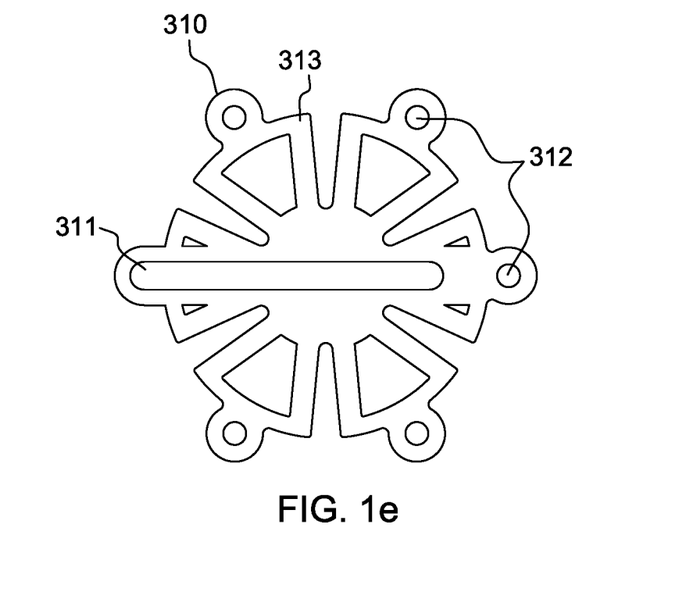
FIG. 1e is a perspective view of another embodiment of a dynamic decompressive cranial fixation device according to the present disclosure.

FIG. 1*e* illustrates another embodiment of a dynamic cranial stabilization and/or fixation device 310 and related method. The cranial fixation device 310 is similar to the cranial fixation devices 10, 110 and 210 described above and includes like elements and like features and/or capabilities, and therefore includes like reference numerals preceded by the numeral "3" to indicate such likenesses.

The cranial fixation device 310 is configured similar to a burr hole covering with one elongated or extended dynamic aperture 311 and a plurality of fixations apertures 312. In some embodiments the plurality of fixations apertures 312 may be formed on, coupled to, or extended from wings or extension segments 313 extending from the middle portion of the device 310, as shown in FIG. 1*e*. Similarly, as also shown in FIG. 1*e*, the extended dynamic aperture 311 may be provided by, at least in part, one or more wing or extension segment 313 extending from the middle portion of the device 310. In some embodiments, the wings or extension segments 313 may include a space between adjacent wings or extension segments 313, and/or a space or aperture extending therethrough in addition to the plurality of fixations apertures 312.

In some embodiments the plurality of fixations apertures 312 may be positioned about a radius or arc, as shown in FIG. 1*e*. In addition, the extended dynamic aperture 311 such that one end of the aperture 311 may be aligned in the arced or radiused configuration of the fixations apertures 312 such that the entirely of the apertures forms an arced or radiused configuration. Further, the fixations apertures 312 and one edge or portion of the extended dynamic aperture 311 may form a substantially circular or elliptical pattern or configuration. The fixations apertures 312 and one edge or portion of the extended dynamic aperture 311 may also be spaced about 60 degrees form one another, such as about the center of the device 310. The fixations apertures 312 and one edge or portion of the extended dynamic aperture 311 may further be positioned about the periphery of the device 310. Additionally, the dynamic aperture 311 may be extended into the center or middle portion of the device 310, as shown in FIG. 1e.

As discussed above, the attachment mechanism or means may be positioned through at least one of the fixations apertures 312 to substantially fix the device 310 to one or more cranial bone. Further, one or more attachment mechanisms may be fixed to a bone flap through the dynamic aperture 311. In this way, the device 310 may allow for the dynamic controlled movement of the bone flap with respect to at least the one or more cranial bones. In some embodiments, at least one of the fixations apertures 312 may be utilized via an attachment mechanism to fix the bone flap to the device 310, and thereby to the one or more cranial bones are fixed to the device 310 via at least one of the remaining fixations apertures 312 (e.g., after intracranial pressure subsides). In some embodiments, the material of the device 310 may be configured to at least partially cover a burr hole or other defect when attached to a patient via the fixations apertures 312 and dynamic aperture 311.

Figure 1F:
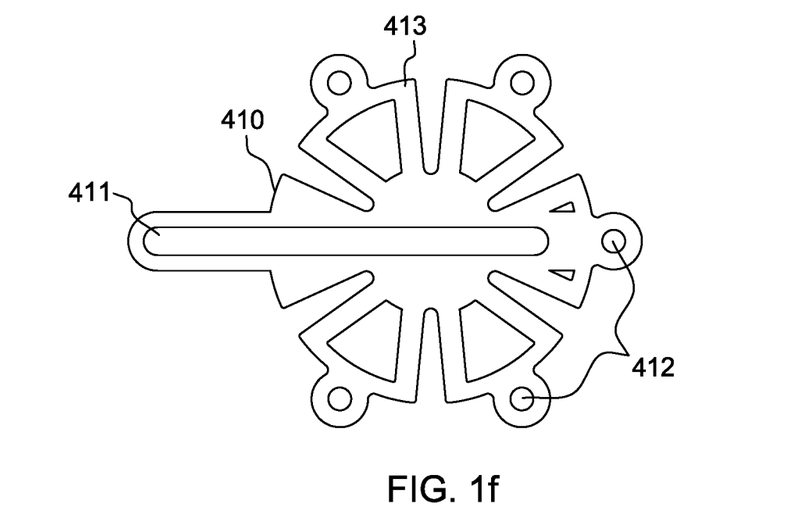
FIG. 1f is a perspective view of another exemplary embodiment of a dynamic decompressive cranial fixation device according to the present disclosure.

FIG. 1f illustrates another embodiment of a dynamic cranial stabilization and/or fixation device 410 and related method. The cranial fixation device 410 is similar to the cranial fixation device 310 described above and therefore like reference numerals preceded by the numeral "4" as opposed to the number "3" is used to indicate like elements. One difference of device 410 as compared to device 310 is the configuration of the dynamic aperture 411. As shown in FIG. 1f, the dynamic aperture 411 of device 410 extends from the center or middle portion of the device 410 to an extension or "tail." In some embodiments the extension portion of the dynamic aperture 411 extends further than the periphery of the fixation apertures 412 from the center or middle portion of the device 410. In addition, the dynamic aperture 411 may allow further translation or movement of the bone flap than the dynamic aperture 311 of device 310 of FIG. 1e.

Figure 2A:
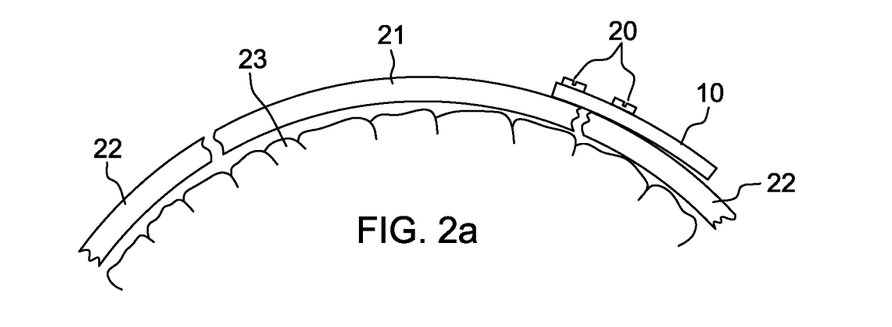
FIG. 2a is a side cross-sectional view of any of the dynamic decompressive cranial fixation devices of FIGS. 1a-f coupled to a bone flap of a cranium without intracranial pressure according to the present disclosure.
Figure 2B:
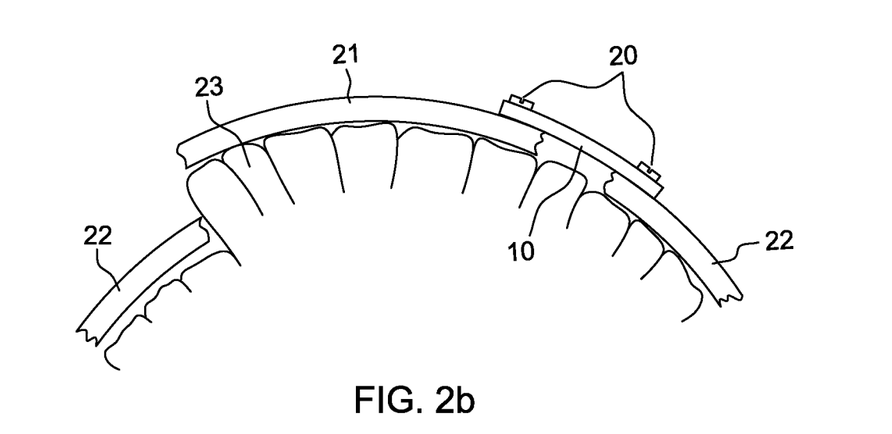
FIG. 2b is a side cross-sectional view of any of the dynamic decompressive cranial fixation devices of FIGS. 1a-f coupled to a bone flap of a cranium with intracranial pressure according to the present disclosure.

FIGS. 2a & 2b illustrate cross-sectional views of the device 10 of FIG. 1a implanted, installed, coupled, fixed or otherwise in use on a patient's skull 22. However, any of devices 110, 210, 310 or 410 may be substituted for device 10 of FIG. 1 as one of ordinary skill in the art would appreciate. As shown in FIG. 2a, the device 10 may be coupled to a skull bone via one or more attachment member 20. In the embodiment shown in FIG. 2a, a fixation aperture is utilized via at least one attachment member 20 to fix the device 10 to a bone flap 21 positioned over the patient's brain 23. As shown in FIG. 2a, in a non-extended state the bone flap 21 and the cranium or skull 22 may be adjacent and/or substantially aligned. Such a configuration, arrangement or state may occur immediately after placement of the device 10 and/or after intracranial pressure of the brain 23 has dissipated or decreased. The bone attachment mechanism or member 20 coupled to the cranium 22 via a dynamic aperture may be relatively proximate the attachment mechanism or member 20 coupled to the bone flap 21 via a fixation aperture in the state shown in FIG. 2a.

FIG. 2b illustrates the brain 23 and bone flap 21 in a pressurized, swollen or extended state as compared to the state shown in FIG. 2a. As shown in FIG. 2b, the device 10 is in an extended configuration, arrangement or state to allow for the brain 23 to swell to alleviate, decrease or otherwise accommodate for intracranial pressure. Specifically, the pressure within the brain 23 exerts a force against the bone flap 21 and, thereby, the device 10 secured thereto via attachment mechanism or member 20 passing through the at least one fixation aperture of the device 10. The bone flap 21 and the device 10 are fixed to the bone flap 211 and may translate due to the intracranial pressure with respect to the adjacent cranium 22 and the attachment mechanism or member 20 passing through at least one fixation mechanism of the device 10 and into the cranium 22, as shown in FIG. 2b. As also shown in FIG. 2b, the device 10 may be fixed to a curved or arcuate portion of the cranium 22, such that as the device translates along the dynamic aperture (the direction thereof determined, e.g., by the configuration of the dynamic aperture and orientation of the device 10 on the cranium 22 and bone flap 21), the bone flap 21 is translated away from brain 23 such that additional space is created between the brain 23 and the interior surface of the bone flap 21.

In some embodiments (not shown), the device 10 (and any alternative embodiment described herein or supported hereby) may include one or more stationary plate, kick plate or the like to, for example, prevent the bone flap 21 from translating below the cranium 22 about the bone flap 21 after the swelling or intracranial pressure of the brain 23 resolves, reduces or is substantially eliminated. For example, the bone flap 22 may include one or more plate fixed thereto that extends past the periphery of the bone flap 21. As swelling subsides, the at least one plate may contact the skull 22 when the bone flap 21 and the skull 22 are approximated during the resolution phase of brain 23 swelling to prevent the bone flap 21 from moving further inward.

Figure 3A:
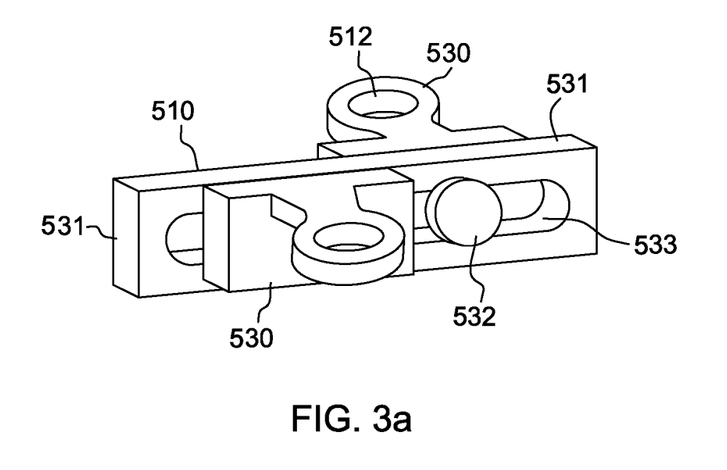
FIG. 3a is a perspective view of another embodiment of a dynamic decompressive cranial fixation device according to the present disclosure.
Figure 3B:
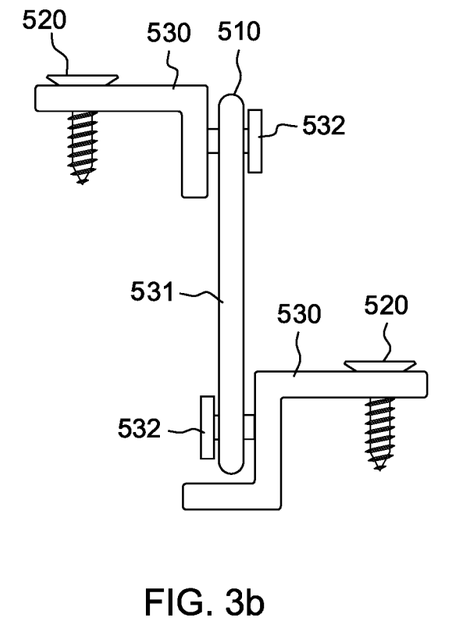
FIG. 3b is a side view of the dynamic decompressive cranial fixation device of FIG. 3a according to the present disclosure.

FIGS. 3a and 3b illustrate another embodiment of a dynamic cranial stabilization and/or fixation device 510 and related method. The cranial fixation device 510 is similar to the cranial fixation devices 10, 110, 210, 310 and 410 described above and includes like elements and like features and/or capabilities, and therefore includes like reference numerals preceded by the numeral "5" is used to indicate like elements. As shown in FIGS. 3a and 3b, the cranial fixation device 510 may include a connector member 531 with an elongated aperture 533 extending therethrough along the length of the connector member 531. In some embodiments, the connector member 531 may be an elongated strip of material. The cranial fixation device 510 may also include at least a pair of wing members 530 on opposing sides of the connector member 531 movably coupled to the connector member 531. As shown in FIGS. 3a and 3b, the each wing member 530, 530 may be movable within the elongated aperture 533 of the connector member 531. In some embodiments, the wing members 530, 530 may include a pin member 532 that extends from the wing member 530 and passes through the elongated aperture 533 of the connector member 531. The pin member 532 of the wing members 530, 530 may pass through the elongated aperture 533 of the connector member 531 such that the pin member 532 may be capable of translating or sliding along the elongated aperture 533. Further, the pin member 532 may be capable of rotating within the elongated aperture 533, such that wing members 530, 530 are capable of rotating with respect to each other and the connector member 531.

As shown in FIGS. 3a and 3b, the pin member 532 of the wing members 530, 530 may include an expanded head or stop mechanism positioned on an opposing side of the connector member 531 and the elongated aperture 533 to which the wing member 530 is positioned. The head portion of each pin member 532 may be sized and/or shaped such that the pin member 532 is prevented from passing back through the elongated aperture 533 of the connector member 531 (e.g., larger than the elongated aperture 533). Further, as shown in FIGS. 3a and 3b, the wing members 530, 530 themselves may be sized and/or shaped such that the wing member 530 is prevented from passing through the elongated aperture 533 of the connector member 531. In this way, as shown in FIGS. 3a and 3b, the wing members 530, 530 may be movably coupled to the elongated aperture 533 of the connector member 531. Stated differently, the wing members 530, 530 may be freely movable with respect to one another at least about two planes or directions, and the connector member 531 may extend between the wing members 530, 530. In some embodiments the connector 531 can slide along each wing member 530, 530 and thereby allowing the distance between the wing members 530, 530 to be adjusted.

As shown in FIGS. 3a and 3b, the wing members 530, 530 may include a fixation aperture 512 for mating with an attachment member 520. In some embodiments, the fixation aperture 512 of the wing members 530, 530 may extend way from the connector member 531 and the opposing wing member 530. In some embodiments, each wing member 530, 530 may include an L-shape, such that the fixation aperture 512 is formed through one leg of the L-shape and the pin member 532 extends from the other leg of the L-shape.

In use, one wing member 530 may be firmly attached or fixed to a bone flap via a bone attachment mechanism 520, and the other wing member 530 may be firmly attached or fixed to the skull or cranium with another bone attachment mechanism 520. The bone flap may move with respect to the skull or cranium as the wing members 530, 530 rotate and/or translate in the elongated aperture 533 of the connector member 531 and with respect to one another, as shown in the differing orientations of FIGS. 3a and 3b. In some embodiments, when attached to a skull and bone flap, the connector member 531 may be positioned between the skull and bone flap, as the wing members 530, 530 may attach to the edge of the skull and bone flap and "wrap" around the edge.

Figure 4A:
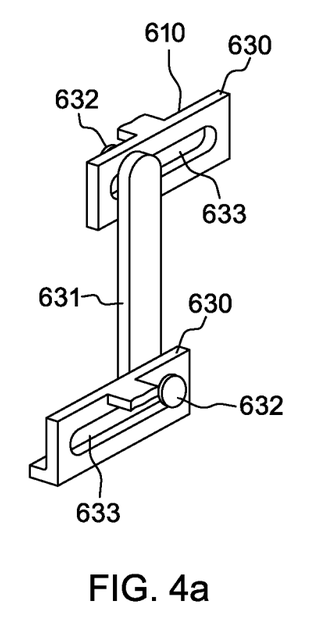
FIG. 4a is a perspective view of another embodiment of a dynamic decompressive cranial fixation device according to the present disclosure.
Figure 4B:
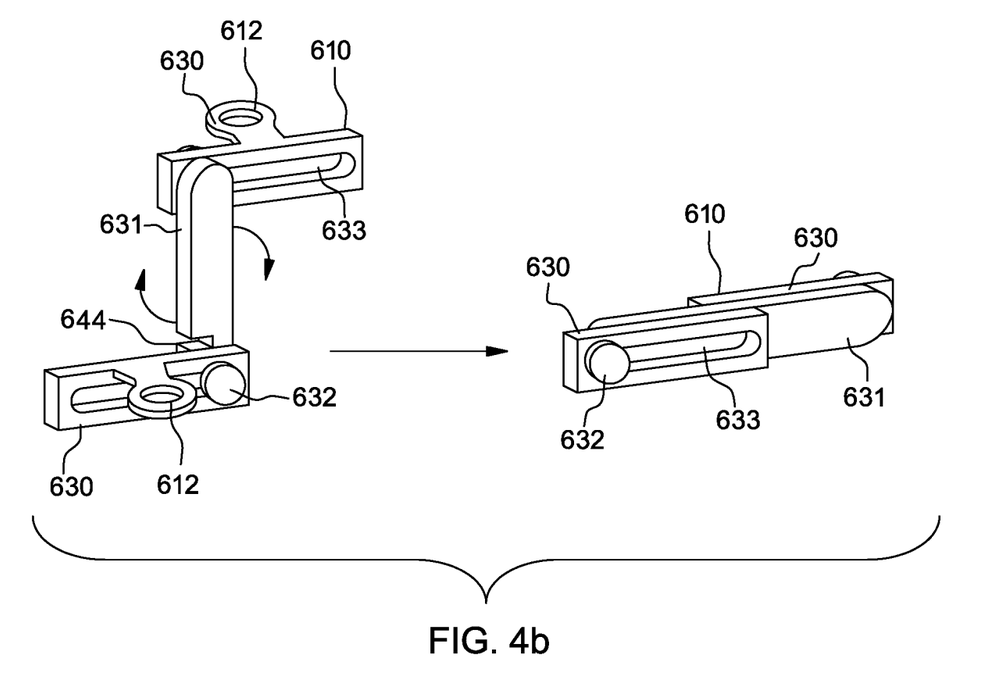
FIG. 4b is a perspective view of the dynamic decompressive cranial fixation device of FIG. 4a illustrating exemplary extended and retracted states of the device according to the present disclosure.

FIGS. 4a and 4b illustrate another embodiment of a dynamic cranial stabilization and/or fixation device 610 and related method. The cranial fixation device 610 is similar to the cranial fixation device 510 described above and includes like elements and like features and/or capabilities, and therefore includes like reference numerals preceded by the numeral "6," as opposed to "5," is used to indicate like elements. One difference between fixation device 610 and fixation device 510 includes the location of the pin members 632 and extended aperture 633. As seen in FIGS. 4a and 4b, the pin members 632 may extend from each end of the connector member 631. Further, as also shown in FIGS. 4a and 4b, each wing member 630, 630 may include an extended aperture 633, 633 for mating with the pin members 632, 632 at each end of the connector member 631. It is noted that each wing member 630 of FIG. 4b is only partially illustrated to demonstrate the retracted state.

Another difference between fixation device 610 and fixation device 510 is the inclusion of at least one stop mechanism 644, as seen in FIG. 4b. In some embodiments, the device 610 may include a stop mechanism 644 that limits the relative movement of the wing members 630, 630 with respect to one another. For example, as shown in FIG. 4b, in some embodiments the stop mechanism 644 may include a protrusion or projection from one of the connector member 631 and/or the wing members 630, 630 that interacts with the other of the connector member 631 and the wing members 630, 630 to limit the angulation or orientation between the connector member 631 and a particular wing member 630 (i.e., limit the movement provided by the pin member 632 and the extended aperture 633). In addition, the stop mechanism 644 may include an aperture, cavity, cutaway or other feature configured to mate with the protrusion or projection of the stop mechanism 644. Further, the device 610 may include a stop mechanism 644 associated with each wing member 630 and the connector member 631 to limit the maximum angle of orientation between the components to about 90 degrees. Additionally, the stop mechanism 644 may limit the amount of movement between the bone flap and the cranium or skull by limiting the amount of movement of the wing members 630, 630 with respect to one another from the fully collapsed position of the device 610 (e.g., see the right side of FIG. 4b). Further, the stop mechanism 644 may allow for the device 610 to move in a reverse direction (as compared to the direction it previously moved during brain edema) to allow the bone flap to move inward towards the skull during resolution of brain edema, as exhibited in FIG. 4b.

Figure 5A:
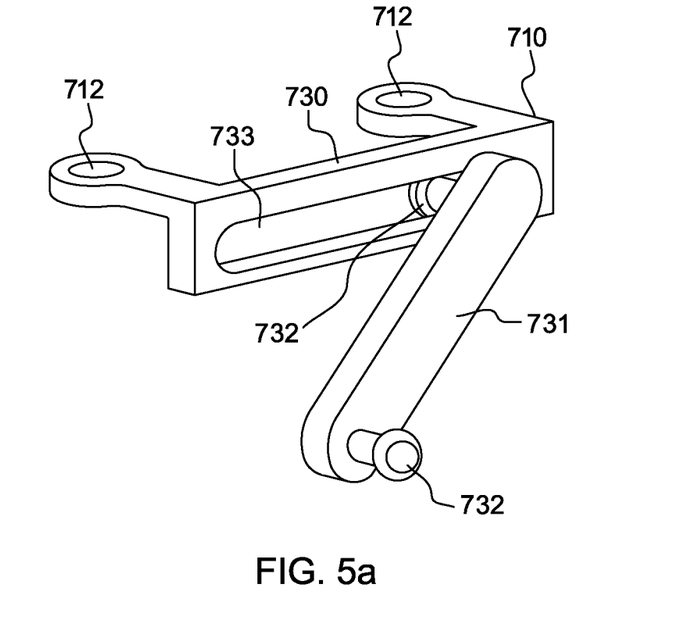
FIG. 5a is a perspective view of a portion of another embodiment of a dynamic decompressive cranial fixation device according to the present disclosure.
Figure 5B:
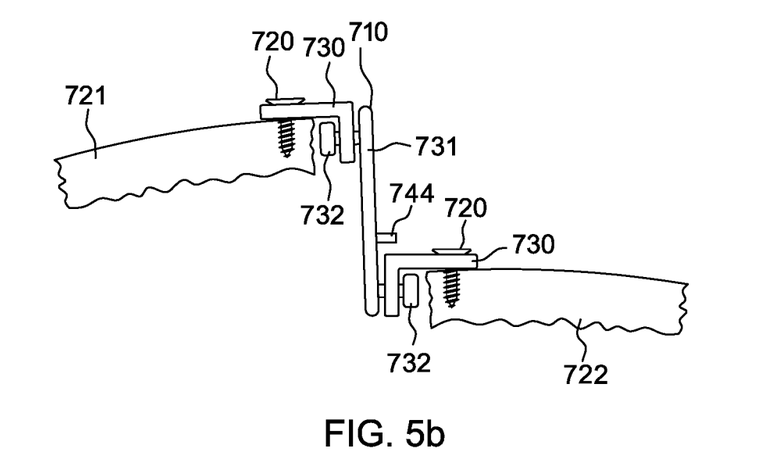
FIG. 5b is a side cross-sectional view of the dynamic decompressive cranial fixation device of FIG. 5a coupled to a bone flap of a cranium with intracranial pressure according to the present disclosure.
Figure 5C:
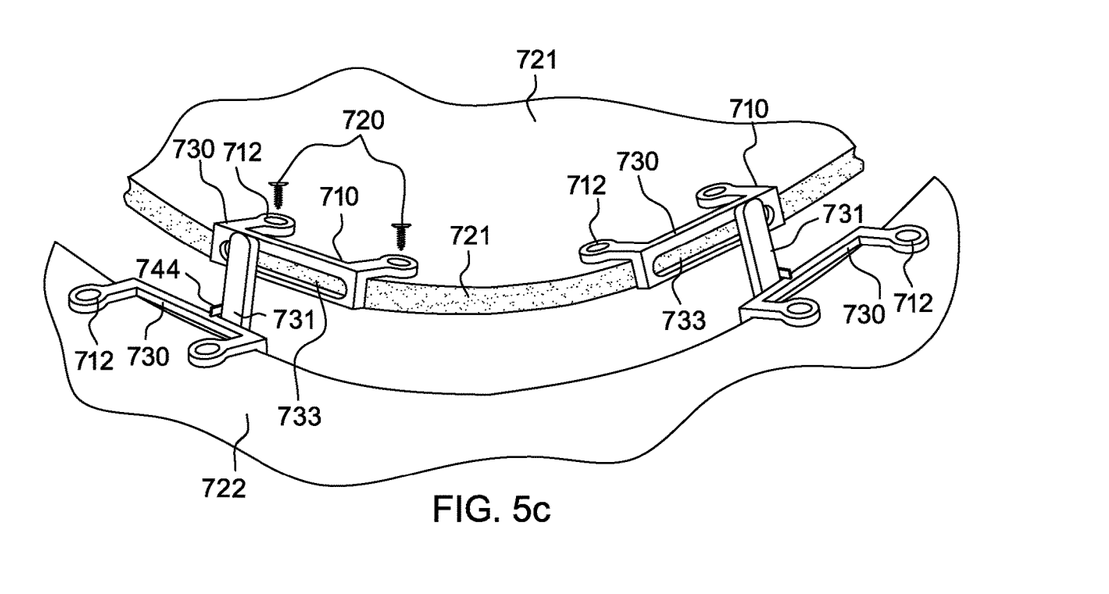
FIG. 5c is a perspective view of the dynamic decompressive cranial fixation device of FIG. 5a coupled to a bone flap of a cranium with intracranial pressure according to the present disclosure.

FIGS. 5a, 5b and 5c illustrate another embodiment of a dynamic cranial stabilization and/or fixation device 710 and related method. The cranial fixation device 710 is similar to the cranial fixation device 610 described above and includes like elements and like features and/or capabilities, and therefore includes like reference numerals preceded by the numeral "7," as opposed to "6," is used to indicate like elements. One difference between fixation device 710 and fixation device 610 includes the fixation apertures 712 of each wing member 730. As shown in FIGS. 5a, 5b and 5c, in some embodiments each wing member 730 includes at least two fixation apertures 712, 712 configured to receive two attachment mechanisms 720, 720. In this way, as shown in FIG. 5c, two attachment mechanisms 720, 720 may be utilized to fix a wing member 730 to the bone flap 721, and two attachment mechanisms 720, 720 may be utilized to fix another wing member 730 to the cranium or skull 722.

As also shown in FIG. 5c, in some embodiments two or more devices 710 may be utilized such that a wing member 730 of two devices 710, 710 may be installed via at least two attachment members 720, 720 on the same edge of the bone flap 721, and the other wing member 730 of the two devices 710, 710 may be installed via at least two attachment members 720, 720 on the same edge (e.g., about the same side of the bone flap 721 or substantially adjacent one another) of the cranium or skull 722. In some alternative embodiments (not shown), two devices 710 may be used on opposite or substantially opposing sides of the bone flap 721, or in any other arrangement about the perimeter of the bone flap 721.

Figure 6A:
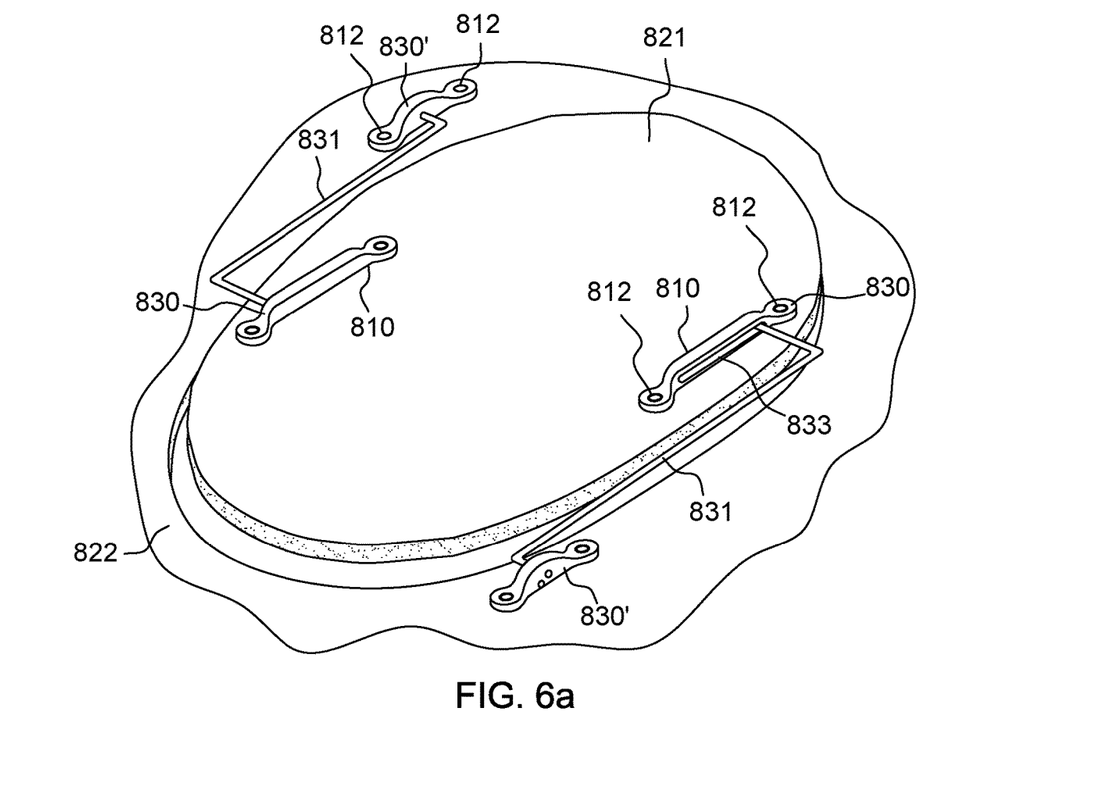
FIG. 6a is a perspective view of another dynamic decompressive cranial fixation device coupled to a bone flap of a cranium with intracranial pressure according to the present disclosure.
Figure 6B:
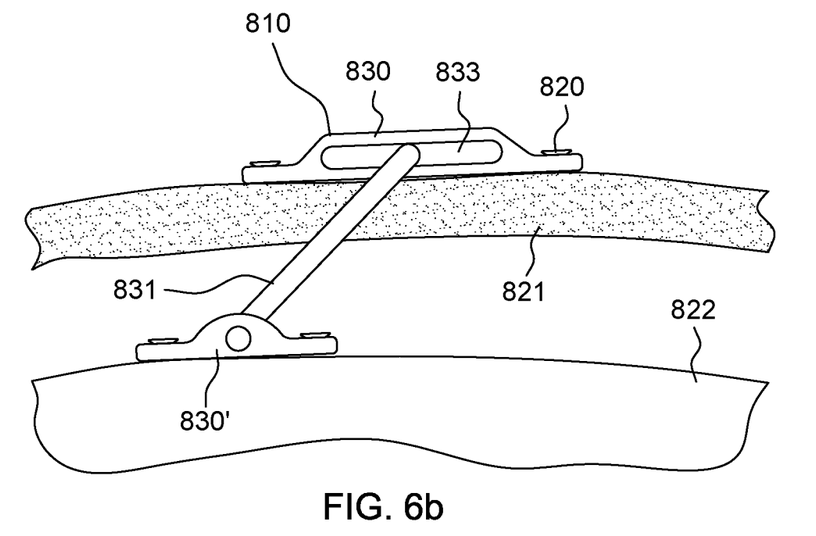
FIG. 6b is a side view of the dynamic decompressive cranial fixation device of FIG. 6a coupled to a bone flap of a cranium with intracranial pressure according to the present disclosure.

FIGS. 6a and 6b illustrate another embodiment of a dynamic cranial stabilization and/or fixation device 810 and related method. The cranial fixation device 810 is similar to the various cranial fixation device embodiments 10, 110, 210, 310, 410, 510, 610, and 710 described above and includes like elements and like features and/or capabilities, and therefore includes like reference numerals preceded by the numeral "8" is used to indicate like elements. As shown in FIGS. 6a and 6b, the cranial fixation device 810 may include a first wing member 830 and a second wing member 830'. In some embodiments, the first wing member 830 may include an elongated or extended aperture, slot, cavity, space, groove or the like 833, and the second wing member 830' may be void of such an elongated aperture 833, as shown in FIGS. 6a and 6b.

As also shown in FIGS. 6a and 6b, in some embodiments the connector member 831 may be coupled to each of the first wing member 830 and the second wing member 830'. In some embodiments, one end or portion of the connector member 831 may be movably coupled with the elongated aperture 833 of the first wing member 830 such that the connector member 831 may rotate with respect to the first wing member 830 and translate along a length of the connector member 831 within the elongated aperture 833. In this way, the elongated aperture 833 may provide at least two planes, axes or directions of movement between the first wing member 830 and the connector member 831. In some embodiments, the interface or connection between the connector member 831 and the first wing member 830 is such that the connector member 831 is capable of translating along and/or within the elongated aperture 833 but is prevented from being removed from the elongated aperture 833 during operation. For example, the connector member 831 may include a mechanism, such as an expansion, lip or a ball-shaped end, which is positioned through the elongated aperture 833 and prevents the connector member 831 from becoming disengaged from the elongated aperture 833.

As shown in FIGS. 6a and 6b, in some embodiments another end or portion of the connector member 831 not coupled to the first wing member 830 may be movably coupled with the second wing member 830'. The connector member 831 may be rotatably coupled with the second wing member 830'. As such, in some such embodiments the connector member 831 may rotate with respect to the second wing member 830'. In this way, the connection between the second wing member 830' and the connector member 831 may provide at least one axis, plane or direction of movement between the second wing member 830' and the connector member 831.

In addition, the connector member 831 may extend between the first wing member 830 and the second wing member 830'. As seen in FIGS. 6a and 6b, in some embodiments the connector member 831 may be "Z" shaped such that the connector member 831 includes two bends, angles, turns, extensions or the like separating three segments, portions, arms or the like. In this way, the connector member 831 may space the first wing member 830 and the second wing member 830' from each other in at least two directions, planes or the like, as shown in FIG. 6a. The connector member 831 may also include two bends or angles such that the ends of the connector member 831 extend in differing directions, such as substantially opposite directions. Further, the connector member 831 may include two ends bent at about 90 degrees such that the ends of the connector member 831 extend at opposite directions.

The connector member 831 may traverse a bone flap-cranium junction or edge. For example, as shown in FIG. 6a, the first wing member 830 and the second wing member 830' may be fixed to the cranium 822 and bone flap 821, respectively (or opposite thereof), and the connector member 831 may traverse the junction of the cranium 822 and bone flap 821. A first segment of the connector member 831 may also extend out from the first wing member 830 in a direction substantially along the axis of rotation between the connector member 831 and the first wing member 830, and/or substantially perpendicular to elongated aperture 833, and traverse the bone flap-cranium junction or edge before turning or bending toward the second wing member 830' adjacent the cranium 822 with a second segment. The second segment may extend to the second wing member 830' before turning or bending toward the second wing member 830' with a third segment in the direction substantially along the axis of rotation between the connector member 831 and the second wing member 830'. In such a way, for example, the connector member 831 may not interfere with or otherwise inhibit the movement of the bone flap 821 away from the cranium 822. In some embodiments, the entirely of each device 810 may be exterior to the cranium 822 and bone flap 821 (as opposed to being partially positioned within the junction of the cranium 822 and bone flap 821, for example). The connector member 831 may allow the bone flap 821 to extend at least partially outwards and separated from the cranium 822 during intracranial pressure, and return to a neutral positioned after intracranial pressure has dissipated.

Figure 7:
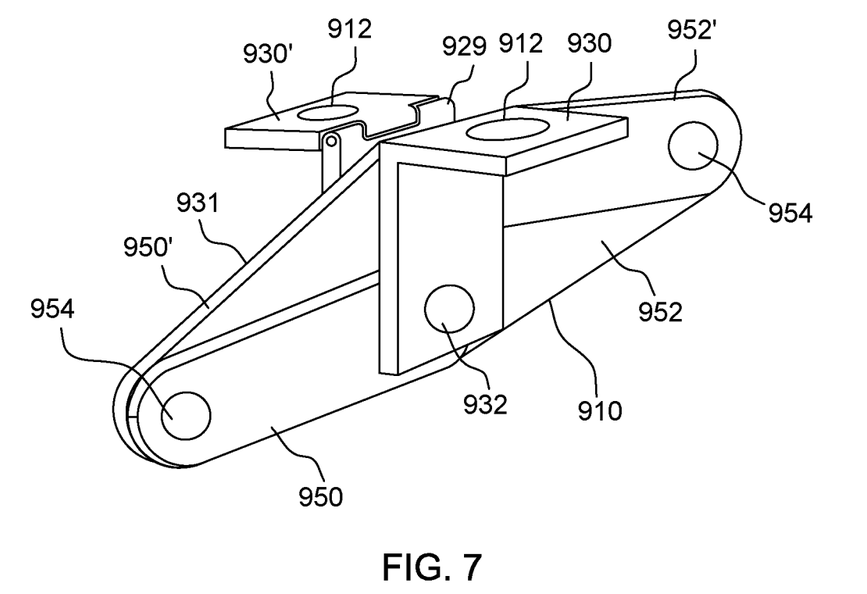
FIG. 7 is a perspective view of another dynamic decompressive cranial fixation device coupled to a bone flap of a cranium with intracranial pressure according to the present disclosure.

FIG. 7 illustrates another embodiment of a dynamic cranial stabilization and/or fixation device 910 and related method. The cranial fixation device 810 is similar to the cranial fixation devices 10, 110, 210, 310, 410, 510, 610, 710 and 810 described above and includes like elements and like features and/or capabilities, and therefore includes like reference numerals preceded by the numeral "9" is used to indicate like elements. As shown in FIG. 7, the cranial fixation device 910 may include a first wing member 930 and a second wing member 930'. The device 910 may also include a connection mechanism 931 that includes two pairs of arms. FIG. 7 shows a first pair of a first arm 950 and a second arm 952 may be coupled rotatably coupled to the first wing member 930 via a rotation mechanism 932. In this way, the first arm 950 and the second arm 952 may be rotatable with respect to the first wing member 930 (and/or vice-versa). Similarly, a second pair of a first arm 950' and a second arm 952' may be coupled rotatably coupled to the second wing member 930' via a rotation mechanism (not shown). In this way, the first arm 950' and the second arm 952' may be rotatable with respect to the second wing member 930' (and/or vice-versa).

As shown in FIG. 7, the first arm 950 of the first wing member 930 and the first arm 950' of the second wing member 930' may be rotatable coupled to one another via a rotation mechanism 954. In some embodiments, the first arms 950, 950' may be rotatable coupled at a position space from their respective wing member 930, 930'. Similarly, as seen in FIG. 7 the second arm 952 of the first wing member 930 and the second arm 952' of the second wing member 930' may be rotatable coupled to one another via a rotation mechanism 954. In some embodiments, the second arms 952, 952' may be rotatable coupled at a position from their respective wing member 930, 930'. The rotation mechanism 954 and/or the rotation mechanism 932 may comprise a hinge pin.

The first and second wing members 930, 930', and the corresponding pairs of first arms 950, 950' and second arms 952, 952' may allow for the first and second wing members 930, 930' to translate away from each other to adjust the distance between the members 930, 930' at least along a first direction. When the first and second wing members 930, 930' are fixed or otherwise coupled to a bone flap and adjacent cranium, the device 910 may thereby allow for the bone flap to move with respect to the cranium in a controlled way.

The second wing member 930' may include a hinge joint 929 such that the fixation aperture 912 of the second wing member 930' may be movable with respect to the other components of the device 910, such as the fixation aperture 912 of the first wing member 930. In this way, when the second wing member 930' is fixed to a bone flap (or a cranium) and the first wing member 930 is fixed to an adjacent cranium (or vice-versa), the joint 929 may allow the bone flap (and device 910, potentially) to change orientation or angle with respect to the cranium or skull.

In some embodiments, the present disclosure provides for a cranial fixation device comprising at least one wing member, with the device fixed to the bone flap and fixed to the skull (e.g., via a bone screw), coupled together via one or more attachment mechanism, either loosely or firmly, such that the distance between the bone flap and skull is adjustable with either one or a combination of the one or more attachment mechanisms. In some embodiments, the one or more attachment mechanisms may include the incorporation of an elongated aperture or opening in the wing member or the attachment mechanisms, and the other of the wing member or the attachment mechanism slidably and/or rotatably coupled with the elongated aperture. In some such embodiments, the at least one wing member includes the elongated aperture and is coupled or fixed to one of the bone flap and skull, and an attachment mechanism is received through the elongated aperture and coupled or fixed the other of the bone flap and skull. In some other embodiments, the device includes at least two wing members, and one or both of the wing members is/are anchored to the skull and the bone flap, and the two wings are connected to each other with a connector mechanism or member. One of the wing members and the connector mechanism may include an elongated aperture, and the other of the wing members and the connector mechanism is slidably and/or rotatably coupled with the elongated aperture. In some other embodiments, the device includes wings coupled or fixed to the skull and the bone flap, and each wing attached to a connector made of a two or more members that may be interconnected with rotation or hinge points to form a linked chain of members, such that this chain of members may be collapsible to a retracted state, such that the members are stacked next to each other with their surfaces juxtaposed, and may be extendable to an extended state such that the members are extended with respect to one another and the skull and the bone flap are spaced distance from one another.

In some embodiments, the devices of the present disclosure may include one or more component including or formed of biologically compatible material that may be metal, titanium, titanium alloy, carbon fiber, polymer of suitable stiffness and strength, and combinations thereof. In some embodiments, the devices of the present disclosure may include one or more component including or formed of a material that is radiolucent.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A dynamic cranial fixation device for coupling a bone flap and a cranium, comprising:
    a connector member being elongated along a first longitudinal direction;
    a first wing member with a bone engagement portion including at least a first aperture configured to accept a bone attachment member therethrough along a third direction to fix the first wing member to one of a bone flap and a cranium, the bone engagement portion of the first wing member extending from only a first side of the connector member; and
    a second wing member with a bone engagement portion including at least a first aperture configured to accept a bone attachment member therethrough along a fourth direction to fix the second wing member to the other of the bone flap and the cranium as compared to the first wing member, the bone engagement portion of the second wing member extending from only a second side of the connector member, wherein the first and second sides of the connector member are opposing sides of the connector member along a second lateral direction that is perpendicular to the first longitudinal direction, the third direction and the fourth direction, and wherein the connector member includes an elongated aperture or a pair of pin members, and wherein each of the first and second wing members include the other of the elongated aperture or one of the pin members of the pair of pin members as compared to the connector member, the elongated aperture extending into the respective member along the second lateral direction, and the pin members being oriented along the second lateral direction, and wherein the pin members are provided within the elongated aperture to movably couple the first and second wing members with the connector member.

2. The dynamic cranial fixation device of claim 1, wherein the connector member includes the elongated aperture, and wherein each of the first and second wing members includes one of the pin members.

3. The dynamic cranial fixation device of claim 1, wherein connector member includes the pair of pin members, and wherein each of the first and second wing members includes the elongated aperture.

4. The dynamic cranial fixation device of claim 1, wherein the first side of the connector member substantially opposes the second side of the connector member.

5. The dynamic cranial fixation device of claim 1, wherein each of the pin members extend through the elongated aperture and includes an enlarged portion that prevents the pin members from becoming removed from the elongated aperture.

6. The dynamic cranial fixation device of claim 1, wherein each of the first wing member and the second wing member include at least a second aperture configured to accept a bone attachment member therethrough.

7. The dynamic cranial fixation device of claim 1, further including a bone attachment member associated with each aperture of the first and second first wing members.

8. The dynamic cranial fixation device of claim 1, wherein each bone engagement portion of the first wing and second wing members includes first and second planar portions that are oriented perpendicular with respect to each other, the first planar portions of the bone engagement portions of the first and second wing members including the first aperture thereof and the second planar portions including the elongated aperture or one of the pin members of the pair of pin members.

9. The dynamic cranial fixation device of claim 1, wherein the pin members and the elongated aperture rotatably couple the first and second wing members and the connector member about an axis of the pin members and translatably couple the first and second wing members and the connector member along the first longitudinal direction.

10. The dynamic cranial fixation device of claim 1, wherein each of the first and second first wing members include first and second portions that are oriented perpendicular with respect to each other, the first portions including the elongated aperture and the second portions including the pin members.

11. The dynamic cranial fixation device of claim 1, wherein at least one of the connector member, first wing member, and second wing member include at least one stop mechanism configured to limit the amount of rotation between at least one of the first and second wing members and the connector member about an axis of the respective pin member thereof.

12. The dynamic cranial fixation device of claim 1, wherein the first wing member and the second wing member are configured to fix to the bone flap and the cranium such that when the first wing member and the second wing member are fixed to the bone flap and the cranium, respectively, at least a first portion of the connector member is adjacent an exposed edge of one of the bone flap and the cranium, and at least a second portion of the connector member is adjacent an exposed edge of one the other of the bone flap and the cranium.

13. A dynamic cranial fixation device for coupling a bone flap and a cranium, comprising:
a connector member being elongated along a first longitudinal direction and including a first longitudinal end and a second longitudinal end;
a first wing member with a first pair of apertures configured to accept a bone attachment member therethrough along a second direction to fix the first wing member to a cranium, the first wing member being rotatably coupled to the first longitudinal end of the connector member and fixed to the connector member along the first direction, and extending from only a first side of the connector member; and
a second wing member with a second pair of apertures configured to accept a bone attachment member therethrough along a third direction to fix the second wing member to a bone flap, the second wing member including an elongated aperture and extending from only a second side of the connector member,
wherein the first and second sides of the connector member are opposing sides of the connector member along a fourth lateral direction that is perpendicular to the first longitudinal direction, the second direction and the third direction, and
wherein the second longitudinal end of the connector member extends into the elongated aperture of the second wing member along the fourth lateral direction to movably couple the second wing member with the connector member.

14. The dynamic cranial fixation device of claim 13, wherein the second longitudinal end of the connector member extends into the elongated aperture of the second wing member to rotatably and translatably couple the second wing member with the connector member.

15. The dynamic cranial fixation device of claim 13, wherein the first wing member and the second wing member are spaced along the fourth lateral direction, the second direction and the third direction in a first orientation of the device.

16. The dynamic cranial fixation device of claim 13, wherein the connector member includes at least three segments including a first segment provided at the first longitudinal end of the connector member that extends substantially along the fourth lateral direction and an axis of rotation of between the first wing member and the connector, a second segment provided at the second longitudinal end of the connector member that extends substantially along the fourth lateral direction and an axis of rotation between the second wing member and the connector, and a third segment extending between the first and second segments along the first longitudinal direction.

17. The dynamic cranial fixation device of claim 16, wherein the device is configured to be coupled to the bone flap and the cranium in a first orientation such that the second segment extends across a junction of the bone flap and the cranium.

18. The dynamic cranial fixation device of claim 16, wherein the first and second segments extend from the third segment in substantially opposing directions.

19. The dynamic cranial fixation device of claim 13, wherein the device is configured to be coupled to the bone flap and the cranium such that the connector member, the first wing member, and the second wing member are positioned exterior to the outer surfaces of the bone flap and the cranium.

20. The dynamic cranial fixation device of claim 13, wherein the second longitudinal end of the connector member extends through the elongated aperture of the second wing member and includes an enlarged portion that prevents the second end of the connector member from becoming removed from the elongated aperture.

* * * * *